US007138139B2

(12) United States Patent
Gauthier et al.

(10) Patent No.: US 7,138,139 B2
(45) Date of Patent: Nov. 21, 2006

(54) TABLET COATING

(75) Inventors: Francois Gauthier, Peymeinade (FR); Yves Duccini, Mouglins (FR); Paul Francis Reeve, Valbonne (FR); Johan Tatin, Grasse (FR)

(73) Assignee: Rohm and Haas Company, Philadelphia, PA (US)

( * ) Notice: Subject to any disclaimer, the term of this patent is extended or adjusted under 35 U.S.C. 154(b) by 308 days.

(21) Appl. No.: 10/687,064

(22) Filed: Oct. 16, 2003

(65) Prior Publication Data

US 2004/0081690 A1 Apr. 29, 2004

(30) Foreign Application Priority Data

Oct. 22, 2002 (EP) ................................ 02292620

(51) Int. Cl.

| | |
|---|---|
| ***A61K 9/46*** | (2006.01) |
| ***C11D 1/08*** | (2006.01) |
| ***C11D 3/37*** | (2006.01) |
| ***C11D 17/00*** | (2006.01) |

(52) U.S. Cl. ..................... 424/466; 510/230; 510/446; 510/476; 510/224

(58) Field of Classification Search ................ 424/466; 510/476, 230, 446, 224
See application file for complete search history.

(56) References Cited

U.S. PATENT DOCUMENTS

| | | | | |
|---|---|---|---|---|
| 3,030,273 | A * | 4/1962 | Zagnoli | 424/477 |
| 4,644,031 | A * | 2/1987 | Lehmann et al. | 524/501 |
| 5,916,866 | A | 6/1999 | Davies et al. | 510/441 |
| 6,087,311 | A | 7/2000 | Van Dijk | 510/294 |
| 6,169,062 | B1 | 1/2001 | Salager et al. | 510/294 |
| 6,221,832 | B1 | 4/2001 | Casteel et al. | 510/446 |
| 6,232,284 | B1 | 5/2001 | Van Dijk et al. | 510/446 |
| 6,355,607 | B1 | 3/2002 | Rahman et al. | 510/446 |
| 6,503,878 | B1 | 1/2003 | Schwartz et al. | 510/446 |

FOREIGN PATENT DOCUMENTS

| | | |
|---|---|---|
| EP | 0238341 B2 | 9/1987 |
| EP | 0481547 A1 | 4/1992 |
| EP | 0522766 A2 | 1/1993 |
| EP | 0799886 A2 | 10/1997 |
| EP | 0812905 A2 | 12/1997 |

OTHER PUBLICATIONS

Campbell, I. Introduction to Synthetic Polymers, Oxford University Press: New York, 1994, pp. 148-150.*

Schüürmann et al. J. Phys. Chem. A. 1998, 102(33), 6706-6712.*

Brown, T. L. et al. Chemistry: The Central Science, 6th edition, Prentice Hall: Englewood Cliffs, NJ, 1994, pp. 630.*

* cited by examiner

*Primary Examiner*—Johann R. Richter
*Assistant Examiner*—James H. Alstrum-Acevedo

(57) ABSTRACT

The present invention relates to water soluble tablet coatings prepared from water soluble, partially and completely neutralized acrylic polymers and at least one film modifying agent.

6 Claims, No Drawings

TABLET COATING

The present invention relates to chemical compositions which are effective in coating tablets. In particular, the coatings comprise film-forming, water soluble polymers that are externally applied to pre-formed tablets.

The rapid development of detergent tablets, water softening tablets, and tablets containing detergents, fabric softeners and a plurality of active ingredients has led to specific requirements and performance characteristics for coating materials used in preparing such delivery devices. An important performance characteristic/requirement of tablet coatings includes rapid dissolution upon contact with an aqueous washing and/or rinsing system allowing the optimal delivery and dispersal of the tablet contents. Tablet coatings, however, must have sufficient mechanical strength to allow tablets to retain their shape and form during manufacture, storage, transport and handling by a user, while protecting and maintaining the integrity of the tablets contents prior to use. The requirement of sufficient mechanical strength of the tablet coating must be balanced by the requirement of rapid dissolution to achieve an appropriate solubility/dispersibility profile. Often times, both desired characteristics are comprised rather than optimized as result of achieving such a balance in preparing a tablet coating. As a consequence, tablets are packaged individually to protect the tablet coating from mechanical damage during manufacture, storage, transport and handling by a user.

Many tablet coatings, therefore, suffer a number of limitations as a result of compromised performance characteristics, which include the tendency for the coating to become damaged during storage, transport and handling, leading to physical degradation of the coating composition. Another limitation is a sensitivity to moisture of certain ingredients encapsulated by the coating, leading to damage or catastrophic failure of the coating from mechanical forces applied to the surface of the tablet coating from swelling of the ingredients, therefore, requiring the coated tablets to be individually packaged or wrapped in water-impervious packaging. Some types of tablet coatings require individual tablet packaging to prevent contact between abrasive or corrosive components of the coating composition or that reside in the tablets contents and sensitive environments of use (e.g. skin). Other tablet coatings result in poor solubility/dispersibility profiles as a result of the coating retarding disintegration of the tablets contents into aqueous solution, while other types of tablet coatings are opaque and do not permit the user to visually inspect the contents of the tablets.

U.S. patent application Ser. No. 09/667,696 discloses coating materials for pellets, characterized in that either one or both of one or more binders and the coating materials comprise one or more polymers having a Tg in the range from −85° C. to +35° C., including multi-phase polymers. The tablet coating provides a pellet having improved diametrical fracture strength under conventional compaction loads. One limitation of the invention is that water insoluble polymers are preferred to prepare pellet coatings, since such polymers are readily dispersed in water. In addition, the pellet coating is a compromise between the desired performance characteristic of rapid dissolution in water and a mechanical strength that is sufficient to protect and maintain the integrity of the pellets contents yet requires individual wrappers to protect the tablet coating from damage.

U.S. Pat. No. 5,916,866 teaches that a detergent tablet having an external coating of a water soluble organic polymer selected from the group consisting of a copolymer of acrylic/methacrylic acid and maleic acid/anhydride, poly (ethylene)glycol (PEG) and a copolymer of vinyl pyrrolidone and vinyl acetate reduces tablet surface friability and increases resistance to tablet abrasion. Moreover, the external coating does not have a deleterious effect on the disintegration of a tablet as measured by the amount of residue remaining after a period of exposure to water. Tablets which have only an external coating of such materials tend to dissolve rapidly once the coating dissolves during a washing cycle, detrimentally altering the tablets solubility/dispersibility profile and that such coatings tend to produce tacky surfaces which require individual packaging after processing. Therefore, it is desirable to prepare alternative types of polymeric, water soluble tablet coatings having sufficient mechanical strength and resistance to abrasion, yet having a minimal effect on the tablet solubility/dispersibility profile and lowering the compaction pressure required to form the tablet.

Inventors have unexpectedly discovered that chemical modification of water soluble polymers conventionally employed as polymeric tablet binders provide tablet coatings having significant utility. Moreover, when such a water soluble polymer formulation is applied in liquid form to a tablet surface after compaction using a conventional coating process and then dried, it forms a protective film coating around the tablet having improved mechanical strength and improved resistance to film degradation during tablet manufacture, storage, transport, and handling by a user; provides a tablet having an improved visual aspect; provides a tablet that can be prepared with no dust generation resulting in a tablet that is safer to handle and which reduces a users contact with oxidizing agents and corrosive ingredients including alkalis, bleaches, enzymes and surfactants; provides a tablet having a minimal effect on the tablet solubility/dispersibility profile as well as lowering the compaction pressure required to form the tablet. Applying coatings of the present invention to pellets or tablets, obviates the above mentioned limitations of tablet coatings disclosed in the prior art. In addition, colors incorporated in tablet coatings of the invention are rendered visually brighter by increased optical transparence of the water soluble polymer compositions, further improving the tablets visual aspect.

Accordingly, a water soluble tablet coating is provided comprising:

(a) at least one film-forming polymer having acidic functional groups and a degree of neutralization ranging from 30 to 100 weight percent, based on the weight of polymer; and (b) at least one film modifying agent.

Accordingly the present invention provides a process for preparing a water soluble tablet coating which comprises the steps of:

(a) applying a film forming polymer in liquid form to a tablet surface; and (b) drying the film to form a protective film coating around the tablet, wherein the film forming polymer formulation comprises at least one film-forming polymer having acidic functional groups and a degree of neutralization ranging from 30 to 100 weight percent, based on the weight of polymer and at least one film modifying agent.

Tablets refer to any composite or matrix of compacted solids, particles, semi-solids, solids incorporating liquids and encapsulated liquids that take the form of solid objects including, but not limited to, pellets, tablets, bricks, bars, granules, balls, blocks, capsules, containers and combinations thereof. The matrix or composite may be heterogeneous or homogeneous in nature and is often both chemically and physically heterogeneous. In a heterogeneous tablet, the matrix or composite contains particles of different sizes or morphologies that may or may not be visually discernable. Visual contrast may be enhanced in a tablet by adding colored particles or encapsulated liquids that are colored. Typical particulate compositions which are compacted to prepare tablets range in size from 100 to 3000 μm. The tablet may comprise a distribution of particles of various sizes, including particles having sizes ≦200 μm, referred to as fines. The tablet may also contain coated particles that result from agglomerating, mixing or any other suitable physical/chemical association of materials using standard processing techniques including, but not limited to, solution coating, dip coating, spraying, spray-drying, fluid bed mixing, coacervation and combinations thereof. The compacted particles may have, in principle, any bulk density. Particles having high bulk densities (≧300 g/L) are usefully employed in the present invention due to their tendency to exhibit disintegration and dispersion problems.

Tablets employed in the accordance with the present invention include at least one active ingredient. Typical examples of active ingredients include, but are not limited to detergents, water softeners, fabric softeners, disinfecting agents, surfactants bleaching agents, water treatment agents, dispersing agents, disintegrating agents, biocides, agrochemicals, pharmaceuticals and combinations thereof. The use of chemical compositions in tablet form is well know, for example, in the field of medicine and agriculture and more recently other areas such as in detergent applications, where they can be used for delivering unit doses of compositions used for dishwashing, fabric washing or other fabric care uses. Alternatively they can be used for dispensing disinfectants or sanitizing agents of various kinds, including oxidant release tablets or formulated biocides for applications including water treatment use or for antimicrobial protection of industrial, domestic or municipal installations. Typical examples of active ingredients and additives comprising a tablet are described in U.S. Pat. No. 5,916,866.

Tablet coatings usefully employed in accordance with the invention are water soluble, film-forming polymers that are capable of forming a continuous layer or a plurality of layers on the tablet surface. The film-forming properties of the water soluble polymer are altered using one or more film modifying agents. Accordingly, the polymers are prepared from hydrophilic and/or hydrophobic acid containing monomers. The resulting polymers have a glass transition temperature (Tg) ranging from 35 to 120° C. and have a weight average molecular weight ranging from 10,000 to 120,000. It is necessary for the polymer to be partially or completely neutralized in order for it to have water solubility. The film forming polymers form water soluble coatings that are smooth, continuous, not friable and do not exhibit significant tack.

The polymers usefully employed in the invention are described in European Pat. No. EP 0 812 905 A2. The polymers are produced by conventional emulsion polymerization and have acid functional groups which can be neutralized using one or more bases either partially or completely in order to give them varying degrees of water solubility. The degree of neutralization is one of the parameters which influences the water solubility of the resulting film. The degree of neutralization of the polymers ranges from 30 to 100 weight percent, based on the weight of polymer. Acid functional groups include, but are not limited to, acrylic acid, methacrylic acid, itaconic acid, and hydroxyalkyl(meth)acrylic acid, and maleic acid. The quantity of acid functional s in the polymer is from 5 to 60 weight %, based on the total weight of the polymer, preferably from 10 to 40 weight %. The remainder of the composition comprises suitable monomers to provide the film with a balance of film integrity, rigidity and hydrophilicity, and is selected from one or more of the following: $C_1$–$C_{18}$ alkyl (meth)acrylates, $C_1$–$C_{18}$ hydroxyalkyl(meth)acrylates and styrene. The term (meth)acrylate refers to acrylate or methacrylate.

Bases are used to partially or completely neutralize the polymer before application to the tablet. Typically, the degree of neutralization of the polymer is between 30 and 100 weight percent, based on the weight of the polymer. The preferred degree of polymer neutralization is between 50 and 80 wt. %.

In a separate embodiment of the invention, an excess of base is required for water soluble polymers used to coat effervescent tablets. Effervescing tablets refer to tablets having an effervescing agent as an active ingredient whose effervescence is induced by the action of an acid or acidic functional groups of a polymer in aqueous solution. Typical effervescing agents include for example carbonate salts, bicarbonate salts and combinations thereof. It is preferred that the water soluble polymer coating is over neutralized, such that an excess of neutralizing base is added to the acid containing polymer over and above the stoichiometric quantity required for complete neutralization of the acid containing polymer. Over neutralization inhibits the localized chemical reaction of the acidic functional groups of the polymer on the carbonate/bicarbonate within the area of application of the water soluble coating to the tablet, thereby inhibiting effervescence during the coating of such tablets.

Suitable neutralizing bases include, but are not limited to, alkali metal hydroxides such as sodium hydroxide and potassium hydroxide, primary amines such as ethanolamines, monoethanolamine, monoisopropanolamine, secondary amines such as aminomethylpropanol, and tertiary amines such as triethanolamine.

The neutralized polymer composition should be adjusted such that the viscosity of the resulting solution is sufficiently low to allow thin, coherent films to be produced. Viscosities should be less than 1000 mpa·s under the shear rate corresponding to the application process, preferably less than 500 mPa·s, and most preferably less than 200 mPa•s. This can be achieved by the usual means of adjusting the solids content, or adding viscosity control agents such as alcohols, hydrotropes or other appropriate additives. Hydrotropes refer to that certain organic salts that stabilize surfactants in order to allow them to remain soluble. Typical hydrotropes include for example alkyl and aryl carboxylate salts.

In accordance with the invention, one or more film modifying agent(s) is added to the water soluble polymer to provide the resulting coating that is applied to the tablet. The film modifying agents are used to alter chemical/physical properties of the tablet coatings and/or conditions under which the tablet coatings are formed from the polymer emulsion. Typical film modifying agents include, but are not limited to, coalescents, plasticizers, dispersants and combinations thereof. The addition of plasticizers to the neutralized polymers render films and coatings that are more supple, flexible and not friable. The use of non-plasticised films will give rise to more rigid and brittle coatings. An increased degree of flexibility can be brought to the coating material by the inclusion of small levels of plasticizers. Typical examples of plasticizers include for example alkylene glycols such as ethylene glycol, propylene glycol and dipropylene glycol, esters of alkylene glycols, nonionic surfactants, TEXANOL® and combinations thereof. Coalescents are added to the neutralized polymers to permit films and coatings to form at lower temperatures. A number of coalescing agents of the invention also induce greater plasticity into polymer films and coatings. Certain plasticizers employed in the invention also function as coalescing agents. Typical coalescents include, for example, alkyl citrates such as triethyl citrate, alkyl alkoxylates and their corresponding esters, alkyl lactates such as ethyl lactate, alkyl gluconates, fatty alcohols, fatty alcohol derivatives, polyalkylene glycol adducts of hydrophobes, PERAMIN SRA® (available from Perstorp) and combinations thereof. Dispersants refer to water soluble organic compounds having one or more alcohol functions or whose alcohol functions have been partially or completely esterified using water soluble monofunctional or polyfunctional organic acids. Suitable water soluble dispersants include, for example trimethylol propane, neopentyl glycol (dimethyl-2,2-propanediol), hexanediol and combinations thereof.

Other suitable coating polymers used in the present invention comprise polymerized residues of one or more of the following monomers: (meth)acrylic acid, (meth)acrylate esters such as methyl(meth)acrylate, ethyl(meth)acrylate, butyl(meth)acrylate iso-butyl(meth)acrylate or t-butyl (meth)acrylate, 2-ethylhexyl(meth)acrylate, decyl(meth) acrylate iso-bornyl(meth)acrylate, and (meth)acrylate esters of alkylene glycols, polyalkylene glycols and (C1–C30) alkyl substituted polyalkylene glycols including esters of the formula CH2=CR1-CO—O(CH2CH R3O)m (CH2CH2CHR3O)n R2 where R1=H or methyl R2=H or C1–C30 alkyl R3=H or C1–C12 alkyl, m=O-40, n=O-40, and m+n is $\geqq 1$, such as hydroxyethyl(meth)acrylate, hydroxypropyl(meth)acrylate; C(1–30) substituted acrylamides; vinyl sulfonate, acrylamidopropanesulfonate; dimethylaminopropyl(meth)acrylamide, alkyl vinyl ethers, vinyl chloride, vinylidene chloride, N-vinylpyrollidone, allyl containing monomers; aromatic vinyl compounds such as styrene, substituted styrenes; butadiene; acrylonitrile; monomers containing acetoacetoxy functional groups such as acetoacetoxyethyl methacrylate; vinyl esters of saturated carboxylic acid, e.g., acetate, propionate, neodecanoate; acid or base containing monomers such as, for example, (meth) acrylic acid, itaconic acid, maleic acid, fumaric acid, N,N-dimethylaminoethyl methacrylate; or combinations thereof. Additionally, crosslinking and grafting monomers such as 1,4-butyleneglycol methacrylate, trimethylolpropane triacrylate, allyl methacrylate, diallyl phthalate, divinyl benzene, or combinations thereof may be used. As used herein, by "(meth)acrylate" or "(meth)acrylic", we mean either acrylate or methacrylate for "(meth)acrylate" and acrylic or methacrylic for "(meth)acrylic"

The polymers used in the present invention may be made using known techniques, for example, solution, emulsion or suspension polymerisation. It is preferred that they are capable of being isolated in solid form, for example by spray drying. To facilitate this, they may comprise a multiphase polymer, that is, they have at least one phase which is relatively hard compared with another phase. Alternatively, a multiphase polymer dissolved or dispersed in water may also be used.

By "multi-phase" polymer we mean polymer particles with at least one inner phase or "core" phase and at least one outer or "shell" phase. The phases of the polymers are incompatible. By "incompatible" we mean that the inner and the outer phases are distinguishable using techniques known to those skilled in the art. For example the use of scanning electron microscopy and staining techniques to emphasise differences in the phases is such a technique.

The morphological configuration of the phases of the polymers may be for example, core/shell; core/shell particles with shell phases incompletely encapsulating the core; core/shell with a multiplicity of cores; or interpenetrating network particles.

The first phase may comprise a "soft" polymer with a Tg in the range 35 to 120° C. Such inner phase polymers may comprise polymerized residues of one or more of the following monomers: (meth)acrylic acid, (meth)acrylate esters such as methyl(meth)acrylate, ethyl(meth)acrylate, butyl (meth)acrylate iso-butyl(meth)acrylate or t-butyl(meth) acrylate, 2-ethylhexyl(meth)acrylate, decyl(meth)acrylate iso-bornyl(meth)acrylate, hydroxyethyl(meth)acrylate, hydroxypropyl(meth)acrylate; (meth)acrylate esters, for example, where the ester group is a polyalkyleneoxide or a C(1–30)alkoxylpolyalkyleneoxide; C(1–30) substituted acrylamides; vinyl sulfonate, acrylamidopropanesulfonate; dimethylaminopropyl(meth)acrylamide, alkyl vinyl ethers, vinyl chloride, vinylidene chloride, N-vinylpyrollidone, allyl containing monomers; aromatic vinyl compounds such as styrene, substituted styrenes; butadiene; acrylonitrile; monomers containing acetoacetoxy functional groups such as acetoacetoxyethyl methacrylate; vinyl esters of saturated carboxylic acid, e.g., acetate; propionate, neodecanoate; acid or base containing monomers such as, for example, (meth) acrylic acid, itaconic acid, maleic acid, fumaric acid, N,N-dimethylaminoethyl methacrylate. Additionally, crosslinking and grafting monomers such as 1,4-butyleneglycol methacrylate, trimethylolpropane triacrylate, allyl methacrylate, diallyl phthalate, divinyl benzene, or combinations thereof may be used.

The outer phase (sometimes regarded as a "shell" if it encapsulates the inner phase), of the multi-phase polymer may comprise either:

i) a polymer with a relatively high Tg value, for example from +40 to 160° C., which makes the outer phase relatively hard. The outer phase may comprise polymerized residues of one or more of the following monomers: (meth)acrylic acid, (meth)acrylate esters such as methyl (meth)acrylate, ethyl(meth)acrylate, butyl(meth)acrylate iso-butyl(meth)acrylate or t-butyl(meth)acrylate, 2-ethylhexyl(meth)acrylate, decyl(meth)acrylate iso-bornyl (meth)acrylate, hydroxyethyl(meth)acrylate, hydroxypropyl(meth)acrylate; (meth)acrylate esters, for example, where the ester group is a polyalkyleneoxide or a C(1–30) alkoxylpolyalkyleneoxide; C(1–30)alkyl substituted acrylamides; vinyl sulfonate, acrylamidopropanesulfonate; dimethylaminopropyl(meth)acrylamide, alkyl vinyl ethers,, vinyl chloride, vinylidene chloride, N-vinylpyrollidone, allyl containing monomers, sulfonates; aromatic vinyl compounds such as styrene, substituted styrenes; butadiene; acrylonitrile; monomers containing acetoacetoxy functional groups such as acetoacetoxyethyl methacrylate; vinyl esters of saturated carboxylic, e.g. acetate, propionate, neodecanoate; acid or base containing monomers such as, for example, (meth)acrylic acid, itaconic acid, maleic acid, fumaric acid, N,N-dimethylaminoethyl methacrylate; or ii) a polymer with a high acid content, for example, a polymer with from 10 to 60% by weight of the polymer of for example, (meth)acrylic acid, preferably from 10 to 50% methacrylic acid and with a Tg in the range from −30 to >100° C. In some cases, this can give a relatively soft outer phase and is not strictly thought of as a "shell". Suitable outer phase polymers of this type are described in EP-A-576128; and U.S. Pat. No. 4,916,171.

iii) polyvinyl alcohol. This alcohol when used as an outer layer is found to stabilise various copolymers with Tg's in the range from 35 to 120° C., for example, vinyl acetate homopolymer; vinyl acetate/ethylene copolymer; vinyl acetate/ethylene/acrylic acid or ester copolymer; vinyl acetate/acrylic acid or ester copolymer such as but not limited to those disclosed in U.S. Pat. No. 4,921,898 and U.S. Pat. No. 3,827,996.

The aforementioned water soluble polymers can be applied to tablets by any appropriate means, including techniques such as solution coating, spraying, dipping and brushing, in order to give integral, cohesive films which are water soluble, and thus will provide protection of the pellet from attrition during transport and handling, by providing increased cohesion and mechanical strength as well as contributing to protection from deterioration caused by moisture pick-up. The resulting filmed pellets, when the film is correctly formulated, and due to the high solubility of the resulting film, will have only minimal impact on the rate of dissolution of the pellet in the use environment. In order to achieve the desired performance and solubility, the polymer should be partly or completely neutralized.

In one embodiment, inventors have discovered that suitable coatings can be prepared from polymers based on two or more monomers comprising (meth)acrylic acid, maleic acid, itaconic acid, hydroxyalkyl(meth)acrylic acid, alkyl (meth)acrylic acid which impart the desired mechanical properties to the tablets but which subsequently dissolve rapidly once the pellets are placed in their environment of use (e.g. aqueous wash bath). The coating of the invention provides a tablet having an improved visual aspect; provides a tablet that can be prepared with no dust generation resulting in a tablet that is safer to handle and which reduces a users contact with oxidizing agents and corrosive ingredients including alkalis, bleaches, enzymes and surfactants; provides a tablet having a minimal effect on the tablet solubility/dispersibility profile as well as lowering the compaction pressure required to form the tablet. Applying coatings of the present invention to pellets or tablets, obviates the above mentioned limitations of tablet coatings disclosed in the prior art. In addition, colors incorporated in tablet coatings of the invention are rendered visually brighter by increased optical transparence of the water soluble polymer compositions, further improving the tablets visual aspect.

In one preferred embodiment, the tablet coatings have utility in tablets which contain a laundry or dishwashing detergent and/or a hard surface cleaner, referred to collectively as detergent-active compounds. The total amount of binder may be from 0.1 to 25% by weight of the pellet, preferably from 0.5 to 15% and particularly preferably from 1 to 5% by weight of the pellet. Such pellets will typically also contain one or more other ingredients which include builders, suitably in an amount of from 5 to 80 wt. %, preferably from 20 to 80 wt. %; bleaching agents; processing additives; adjuvants; enzymes; scale inhibitors; emulsifiers; surfactants; soaps; dispersants; zeolites; de-greasing agents; anti-foaming agents; phosphates; phosphonates; optical brighteners; fillers; extenders; soil removers; deflocculating agents; anti-coagulants; anti-drift agents; disintegration agents, including for example, water swellable polymers; water entraining agents, such as, cellulose; plasticizers or coalescing agents, for example, alkylene glycol alkyl ethers, aromatic glycol ethers, alkyl polyglucosides, polysiloxanes, alcohols and alkyl ester acetates; diluents and carriers. Some of these other ingredients will also be applicable for use in non-detergent pellets.

The one or more coating materials are applied to the tablet surface after compaction of the tablet by any suitable method. Typical compacting loads for commercial pellets without the binders of the present invention can be up to 5000 pounds. The binders of the present invention allows the same pellet formulation to be formed using lower compacting loads. The actual compacting load needed will vary depending on the size of the particles, and the composition of the inorganic components of the pellet.

The coating materials are applied to the outer surface of the pellets by any known method, for example, coating with molten material or coating with a solution of the coating material, by dipping, spraying or brush painting. Enhanced pellet strength is achieved if the coating material also comprises a dicarboxylic acid, for example oxalic acid, malonic acid, succinic acid, glutaric acid, adipic acid, pimelic acid, suberic acid, azelaic acid, sebacic acid, undecanedioic acid, dodecanedioic acid, tridecanedioic acid and mixtures thereof.

Typically, the amount of coating material applied to a pellet is from 0.1 to 25% by weight of the pellet, preferably from 0.5 to 15% and particularly preferably <5% by weight of the pellet.

The present invention will now be described with reference to the following Examples.

EXAMPLES OF TABLET COATINGS PREPARED FROM FORMULATED POLYMERS

AMP: Amino Methyl Propanol
NaOH: caustic soda
NI: non ionic such as C13/C15+7 EO
TEC: Tri Ethyl Citrate
DPG: Di propylene Glycol

Example 1

Autodish Tablets

Autodish tablets have a two layer structure with a round pellet inserted in one layer, to deliver specific ingredients during the rinse by delayed release. All tests were carried out with a water soluble acrylic polymer (47MMA/25BA18MAA/10HEMA) and various plasticizers and neutralizers at different levels. Dissolution was assessed in a dishwasher with a front window.

| Trial number | Neutralisation (level) | Solids | Plasticiser | Film thickness | Film aspect - results |
|---|---|---|---|---|---|
| 1 | NaOH (100%) | 18.6% | — | 230 µm | Brittle |
| 2 | | | | | |
| 2 | NaOH (100%) | 15.4% | — | 145 µm | Idem |
| 3 | NaOH (100%) | 17.4% | NI (1%) | 145 µm | Nice film, fast dissolution |
| 4 | NaOH (100%) | 15.6% | NI (1%) | 130 µm | Slightly sticky, fast dissolution |
| 5 | NaOH (100%) | 18.7% | TEC (1%) | 200 µm | Nice film, relatively fast dissolution |
| 6 | NaOH (100%) | 15.4% | TEC (1%) | 130 µm | Nice film, fast dissolution |
| 7 | AMP (100%) | 18.4% | — | 185 µm | Nice film, slow dissolution |

-continued

| Trial number | Neutralisation (level) | Solids | Plasticiser | Film thickness | Film aspect - results |
|---|---|---|---|---|---|
| 8 | AMP (100%) | 19.6% | — | 245 µm | Glossy, slow dissolution |
| 9 | AMP (65%) | 18.1% | — | 130 µm | Nice film, slow dissolution |
| 10 | AMP (10%) | 20.3% | NI (1%) | 200 µm | Sticky, fast dissolution |
| 11 | AMP (65%) | 19.3% | NI (1%) | 130 µm | Nice film, slow dissolution |
| 12 | AMP (100%) | 19.9% | TEC (1%) | 215 µm | Glossy, slow dissolution |
| 13 | AMP (100%) | 15.5% | TEC (1%) | 130 µm | Sticky, slow dissolution |
| 14 | AMP (65%) | 19% | TEC (1%) | 130 µm | Nice film, fast dissolution |
| 15 | AMP (100%) | 19.6% | DPG (1%) | 230 µm | Glossy, slow dissolution |
| 16 | AMP (100%) | 15.9% | DPG (1%) | 130 µm | Glossy, sticky, fast dissolution |

The test results indicated that using AMP as a neutralizer affords better quality films. The use of the plasticizer TEC improves drying ability and disintegration vs. NI. Dilution enables better control of film thickness and hence positively affect disintegration rate.

Example 2

Bleach Tablets

These tablets based on a chlorine release agent (calcium hypochlorite, dichloro or trichloro isocyanuric acid and salts) can be much larger compared with detergent tablets especially for those used to sanitize swimming pools.

| Trial number | Neutralisation (level) | Solids | Plasticiser | Film thickness | Film aspect - results |
|---|---|---|---|---|---|
| 1 | AMP (65%) | 19% | TEC (1%) | 110 µm | Good quality, stable over storage |

Example 3

Effervescent Tablets

These tablets show a rapid effervescent effect when placed in contact with water, in order to obtain a fast release of active ingredients. Typical applications are stain removers, bleach activators or water softeners.

| Trial number | Neutralisation (level) | Solids | Plasticiser | Film thickness | Film aspect -results |
|---|---|---|---|---|---|
| 1 | AMP (100%) + addition of NaOH up to pH 10 | 17% | TEC (1%) | — | Immediate effervescence, impossible to apply any coating |
| 2 | AMP (100%) + addition of NaOH up to pH 11.5 | 16% | TEC (1%) | — | Some effervescence, difficulty to obtain film formation. |
| 1 | AMP (100%) + addition of NaOH up to pH 13 | 15% | TEC (1%) | 50 µm | Acceptable quality, film stable over time. |

-

The results indicate that a certain level of over neutralization was necessary to stop the phenomenon of effervescence thus enabling the formation of a coating.

Example 4

Detergent Tablets

Detergent tablets have a two layer structure and exhibit rapid disintegration to ensure dissolution and availability of active ingredients in the early stage of the laundry washing cycle. Dissolution was estimated by putting the coated tablets in the machine drawer.

| Trial number | Neutralisation (level) | Solids | Plasticiser | Film thickness | Film aspect -results |
|---|---|---|---|---|---|
| 1 | NaOH (100%) | 18.8% | — | — | Coating not feasible |
| 2 | NaOH (100%) | 19.8% | NI (1%) | 195 μm | Film becomes britle, slow dissolution |
| 3 | AMP (100%) | 18.7% | — | 120 μm | Good quality, difficult to dry |
| 4 | AMP (100%) | 20.3% | NI (1%) | 160 μm | Good quality, slight cracking over ageing |
| 5 | NaOH (100%) | 17.4% | NI (1%) | 105 μm | Good quality |
| 6 | NaOH (100%) | 15.6% | NI (1%) | 75 μm | Good quality, fast drying and disintegration |
| 7 | AMP (100%) | 16.4% | NI (1%) | 80 μm | Idem |
| 8 | NaOH (100%) | 18.7% | TEC (1%) | 130 μm | Idem, cracking after ageing |
| 9 | AMP (100%) | 19.9% | TEC (1%) | 155 μm | Good quality, fast drying |
| 10 | NaOH (100%) | 15.4% | TEC (1%) | 90 μm | Idem, fast disintegration but cracking over ageing |
| 11 | AMP (100%) | 15.5% | TEC (1%) | 90 μm | Good quality, fast drying and disintegration |
| 12 | NaOH (100%) | 17.2% | TEC (0.5%) | 105 μm | Cracking over ageing |
| 13 | NaOH (100%) | 15.4% | TEC (0.5%) | 80 μm | Idem |
| 14 | AMP (100%) | 19.6% | DPG (1%) | 145 μm | Good quality, difficult to dry |
| 15 | AMP (100%) | 15.9% | DPG (1%) | 90 μm | Idem, film keeps sticky |
| 16 | AMP (65%) | 19% | TEC (1%) | 80 μm | Very good quality, fast drying and disintegration |
| 17 | AMP (65%) | 19.3% | Ni (1%) | 90 μm | Idem |

The results indicated that use of a neutralizer alone leads to difficulties to apply coating or to dry the film and that AMP is overall preferred versus NaOH for both drying ability and cracking resistance of the films and coatings. It was also observed that use of a plasticizer TEC versus NI or DPG promotes better film as far as drying and disintegration rate are concerned and that dilution enables a user to build thinner films which will not retard or compromise disintegration.

We claim:

1. A process for preparing a water soluble tablet coating which comprises the steps of:

(a) applying a water-soluble film forming polymer in liquid form to a tablet surface, the film forming polymer comprising one or more monomers selected from the group consisting of: acrylic acid, methacrylic acid, itaconic acid, and hydroxyalkyl(meth)acrylic acid, maleic acid, alkyl (meth)acrylates, hydroxyalkyl(meth) acrylates and styrene and having acidic functional groups and a degree of neutralization ranging from 30 to 100 weight percent, based on the weight of polymer, wherein the acidic functional groups are neutralized with a secondary amine, and including at least one film modifying agent selected from the group consisting of: triethyl citrate, polyethylene glycol, polypropylene glycol, dipropylene glycol, esters of polyalkylene glycols, polyalkylene glycol adducts, fatty alcohols, alkyl phenols, trimethylol propane, neopentyl glycol, hexane diol, alkyl lactates, ethyl lactate, alkyl citrates, alkyl gluconates and combinations thereof; and (b) drying the film to form a protective film coating around the tablet, wherein the film forming polymer formulation consists essentially of at least one water soluble, film-forming polymer having acidic functional groups and a degree of neutralization ranging from 30 to 100 weight percent, based on the weight of polymer and at least one film modifying agent.

2. Process according to claim 1 wherein an excess of neutralizing base is required for water soluble polymers used to coat effervescent tablets.

3. Process according to claim 1 wherein the film modifying agent is selected from the group consisting of a plasticizer, a coalescent, a dispersant and combinations thereof.

4. The process of claim 3 in which the film modifying agent is a trialkyl citrate or a polyalkylene glycol adduct.

5. The process of claim 4 in which the film modifying agent is triethyl citrate or a polyethylene glycol adduct of a $C_{13}$–$C_{15}$ is alkyl group.

6. The process of claim 5 in which the polyethylene glycol adduct contains about seven moles of ethylene oxide units.

* * * * *